United States Patent
Rosa et al.

(10) Patent No.: US 10,765,412 B2
(45) Date of Patent: Sep. 8, 2020

(54) ENDOSCOPIC INSTRUMENT WITH SUPPORT FOOT

(75) Inventors: Benoît Rosa, Leuven (BE); Benoît Herman, Woluwe-Saint-Lambert (BE); Jérôme Szewczyk, Vienne-en-Arthies (FR); Guillaume Morel, Paris (FR); Clément Vidal, Grenoble (FR); Patrick Henri, Bois Colombes (FR); François Lacombe, Chaville (FR); Jérôme Lopez, Aix-en-Provence (FR)

(73) Assignees: UNIVERSITE PIERRE ET MARIE CURIE (PARIS 6), Paris (FR); CENTRE NATIONAL DE LA RECHERCHE SCIENTIFIQUE, Paris (FR); MAUNA KEA TECHNOLOGIES, Paris (FR); ENDOCONTROL, La Tronche (FR)

( * ) Notice: Subject to any disclaimer, the term of this patent is extended or adjusted under 35 U.S.C. 154(b) by 307 days.

(21) Appl. No.: 14/123,659

(22) PCT Filed: Jun. 25, 2012

(86) PCT No.: PCT/EP2012/062264
§ 371 (c)(1),
(2), (4) Date: Feb. 12, 2014

(87) PCT Pub. No.: WO2013/000873
PCT Pub. Date: Jan. 3, 2013

(65) Prior Publication Data
US 2014/0207150 A1    Jul. 24, 2014

(30) Foreign Application Priority Data
Jun. 29, 2011   (FR) ..................... 11 55827

(51) Int. Cl.
*A61B 1/00* (2006.01)
*A61B 17/00* (2006.01)
*A61B 34/00* (2016.01)

(52) U.S. Cl.
CPC .... *A61B 17/00234* (2013.01); *A61B 1/00089* (2013.01); *A61B 1/00137* (2013.01);
(Continued)

(58) Field of Classification Search
CPC ............. A61B 1/0008; A61B 1/00087; A61B 1/00089; A61B 1/00098; A61B 1/00101;
(Continued)

(56) References Cited

U.S. PATENT DOCUMENTS

2003/0176767 A1* 9/2003 Long .................... A61B 1/0014
600/106
2005/0137453 A1* 6/2005 Ouchi ................ A61B 1/00087
600/106
(Continued)

FOREIGN PATENT DOCUMENTS

EP    1 946 707 A2    7/2008

OTHER PUBLICATIONS

International Search Report for PCT/EP2012/062264 dated Aug. 13, 2012.

*Primary Examiner* — Alexandra L Newton
(74) *Attorney, Agent, or Firm* — Sughrue Mion, PLLC

(57) ABSTRACT

The invention relates to an endoscopic instrument (1) having an elongate body with a distal end (4) designed to be introduced into the body of the patient so as to come into proximity with an internal organ, the distal end carrying a tool (7) for intervention on the internal organ. The endoscopic instrument has a fool (10) rigidly connected to the distal end and designed to bear on the internal organ, and also controllable means (13) for conferring movements on
(Continued)

the tool, at least in directions transverse to a longitudinal axis (X) of the distal end of the endoscopic instrument, when the foot is bearing against the internal organ.

13 Claims, 3 Drawing Sheets

(52) U.S. Cl.
 CPC ........ *A61B 34/70* (2016.02); *A61B 2017/003* (2013.01); *A61B 2017/00238* (2013.01); *A61B 2017/00283* (2013.01); *A61B 2017/00296* (2013.01); *A61B 2017/00331* (2013.01); *A61B 2017/00818* (2013.01)

(58) Field of Classification Search
 CPC .......... A61B 1/018; A61B 2017/00296; A61B 17/00234
 USPC ........................................ 600/106, 107, 127
 See application file for complete search history.

(56) References Cited

U.S. PATENT DOCUMENTS

| | | | |
|---|---|---|---|
| 2006/0254603 A1 | 11/2006 | Edwards et al. | |
| 2007/0112249 A1* | 5/2007 | Yamaya | A61B 1/00098 600/107 |
| 2008/0015569 A1* | 1/2008 | Saadat | A61B 1/0008 606/41 |
| 2011/0060227 A1 | 3/2011 | Saadat | |
| 2012/0035416 A1* | 2/2012 | Fernandez | A61B 1/05 600/102 |

* cited by examiner

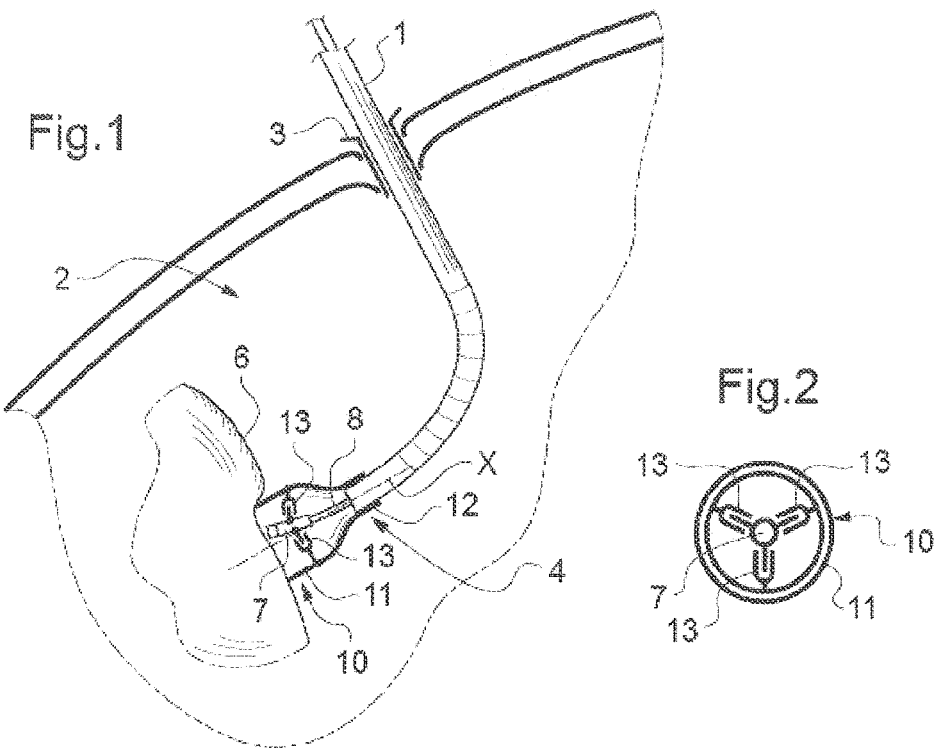
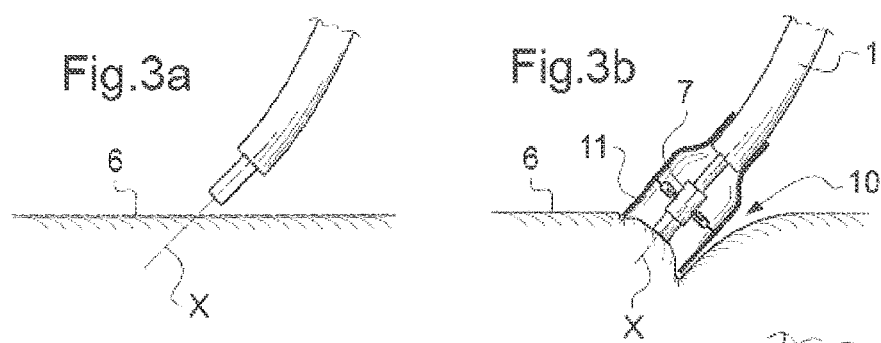
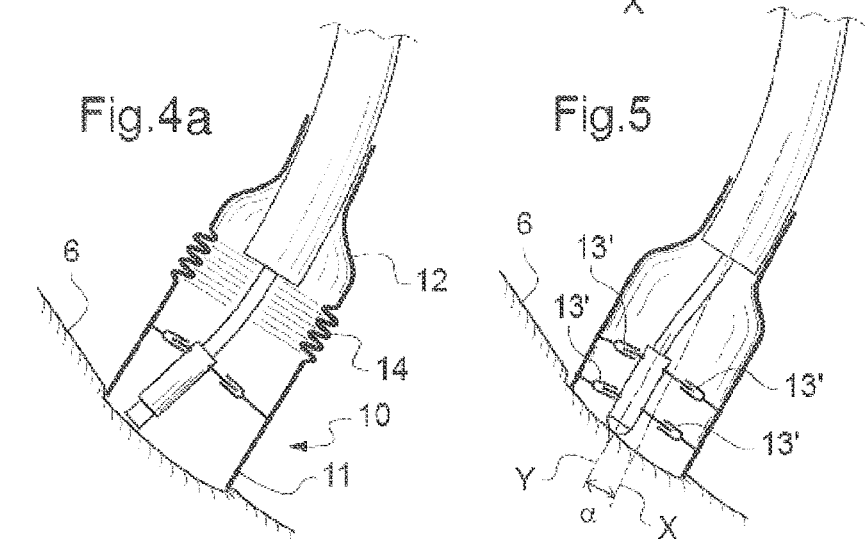

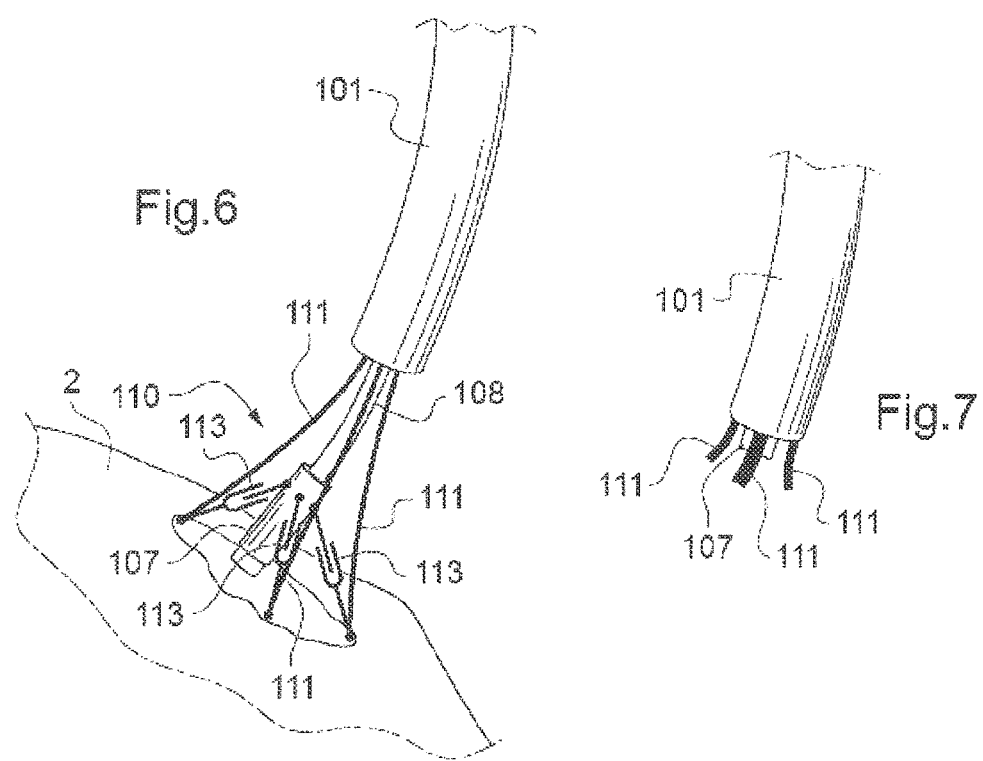
Fig.6
Fig.7
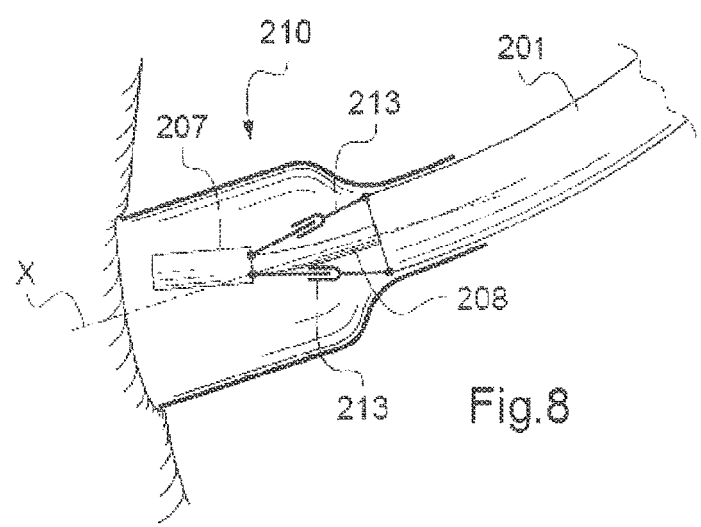
Fig.8

ND0SCOPIC INSTRUMENT WITH SUPPORT FOOT

The invention relates to an endoscopic instrument with a foot.

BACKGROUND OF THE INVENTION

Endoscopic instruments are introduced into the body of the patient, for example into the abdominal cavity, by way of a natural route or an artificial route, for example a cannula, with a view to performing an intervention on an internal organ. This may involve carrying out a biopsy of the organ or inserting a probe into the tissue at a precise location of the internal organ.

It may also involve inspecting a portion of the surface of the internal organ. The endoscopic instrument is then equipped, at its distal end, with a tool, for example a camera or an ultrasound probe. Depending on the circumstances, it may be necessary to ensure positioning and perfect immobility with respect to the internal organ, or it may be necessary to effect a relative movement of the distal end of the endoscopic instrument with respect to the internal organ, in a manner substantially parallel to an outer surface thereof, for example a scanning movement.

To obtain such a movement, the practitioner moves the endoscopic instrument manually, or with robotic assistance, by acting on the part of the endoscopic instrument arranged outside the body. However, such movements are not very precise, and they do not take account of the movements of the patient that induce a movement of the access route, nor of the inherent movements of the organ in the body of the patient.

It has been proposed to use means of immobilizing the organ, specifically a shaping tool which is pressed firmly onto the organ in an attempt to immobilize the latter. However, the immobility of the organ is not guaranteed. In addition, this type of immobilizing device is cumbersome and invasive.

It has also been proposed to perform automatic control of the position of the distal end of the endoscopic instrument relative to the internal organ by means of an on-board camera, the automatic control aiming to annul the relative movements of the distal end of the endoscopic instrument with respect to the internal organ. This method requires the use of real-time video acquisition, and also the use of a complex recursive and adaptive control algorithm.

It has also been proposed to perform automatic control in terms of force, which involves annulling the periodic component of the forces that are applied to the tool by the organ and that are attributable to the physiological movements of the internal organ.

It has also been proposed to equip the distal end of the endoscopic instrument with controlled means of movement which are arranged between the endoscopic instrument and the tool, in order to obtain a movement of the tool with respect to the endoscopic instrument, at least in directions transverse to a longitudinal axis of the end of the endoscopic instrument.

In a first method of use, the endoscopic instrument is immobilized when the tool is at a distance from the organ, and the means of movement are controlled in order to effect a relative movement of the tool with respect to the organ. However, the immobilization of the endoscopic instrument may generate stresses on the access route in the patient, and this may cause the latter discomfort. In addition, the inherent movements of the organ prevent any precise positioning or movement of the tool relative to the organ.

In a second method of use, the tool is brought into contact with the organ, and the endoscopic instrument is left free to move with the patient. However, an adherence may occur between the tool and the organ and cause resistance to the movement of the tool, thus preventing any movement of the latter with respect to the organ or, conversely, giving rise to sudden and uncontrolled slipping.

It is also known from document US 2011/0060227 to equip the distal end of the endoscopic instrument with a foot designed to bear on the internal organ. Shape-memory wires passing all the way through the endoscopic instrument allow the tool to be moved when the foot is bearing against the internal organ.

OBJECT OF THE INVENTION

The object of the invention is to make available an endoscopic instrument with which the tool carried by the instrument can be precisely positioned and/or moved relative to the internal organ to be treated.

SUMMARY OF THE INVENTION

With a view to achieving this object, an endoscopic instrument is made available having an elongate body with a distal end designed to be introduced into the body of the patient so as to come into proximity with an internal organ, the distal end carrying a tool for intervention on the organ, the endoscopic instrument having a foot rigidly connected to the distal end and designed to bear on the internal organ, and also controllable means of movement for conferring movements on the tool, at least in directions transverse to a longitudinal axis of the distal end of the endoscopic instrument, when the foot is bearing against the internal organ. According to the invention, the means of movement have at least one actuator, which is coupled to the tool and which is arranged entirely within the foot.

The foot is brought into contact with the internal organ and is pressed onto the latter with a pressure that is sufficient to prevent any relative movement of the foot with respect to the internal organ. The distal end of the endoscopic instrument then follows the inherent movements of the internal organ, without any relative movement with respect to the latter. The means of movement are then controlled to move the tool relative to the internal organ, the tool being held slightly set back from the surface of the internal organ, or being brought into contact with the latter without causing movement of the foot in relation to the internal organ. It is thus ensured that the physiological movements do not affect the relative position of the tool with respect to the organ, and that the only movements of the tool relative to the internal organ are the controlled movements.

In addition, by placing the actuator entirely inside the foot, it is possible to control very precise movements of the tool. The actuator can in fact then be of a small size and is placed as close as possible to the tool.

Advantageously, according to a preferred embodiment of the invention, the actuator extends between the foot and the tool.

The foot is brought into contact with the internal organ and is pressed onto the latter with a pressure that is sufficient to prevent any relative movement of the foot with respect to the internal organ, such that the internal organ is assumed to be fixed in a reference frame of the foot. Since the actuator extends between the foot and the tool, it is easy to control a precise and stable movement of the tool relative to the foot and therefore relative to the internal organ. Thus, the arrangement of the actuator inside the foot permits even more precise and simple control of a position of the tool relative to the internal organ.

BRIEF DESCRIPTION OF THE DRAWINGS

The invention will be better understood from the following description of particular embodiments of the invention and by reference to the figures of the attached drawings, in which:

FIG. 1 is a schematic representation, in a partial longitudinal cross section, of an endoscopic instrument according to a first particular embodiment of the invention, in position in the abdominal cavity of a patient;

FIG. 2 is a front view of the distal end represented in FIG. 1;

FIGS. 3a and 3b are schematic views allowing comparison between an instrument known per se and an instrument according to the invention which are used in an oblique approach to the internal organ;

FIG. 4a is a view similar to that of FIG. 1 and shows a second particular embodiment of the endoscopic instrument of the invention;

FIGS. 4b and 4c are views similar to that of FIG. 1 and show a variant of the particular embodiment illustrated in FIG. 4a;

FIG. 5 is a view similar to that of FIG. 1 and shows a third particular embodiment of the endoscopic instrument of the invention;

FIG. 6 is a view similar to that of FIG. 1 and shows a fourth particular embodiment of the endoscopic instrument of the invention, the foot being illustrated in the deployed position;

FIG. 7 is a view of the instrument from FIG. 6, the foot being illustrated in the retracted position;

FIG. 8 is a view similar to that of FIG. 1 and shows a fifth particular embodiment of the endoscopic instrument of the invention.

DETAILED DESCRIPTION OF THE INVENTION

Figure 4B:
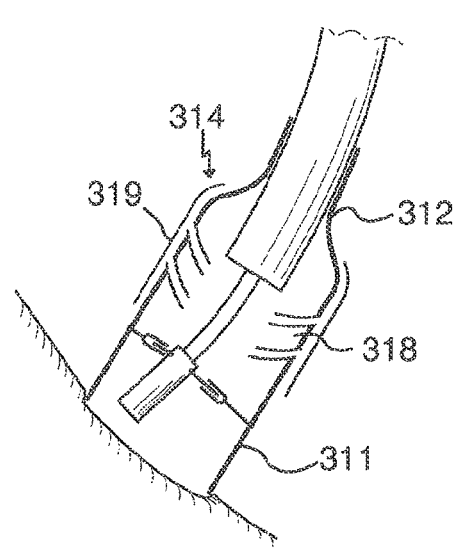

The invention will be described here in connection with an endoscope carrying a medical imaging probe, for example an ultra-high-definition probe from the company called Mauna Kea Technologies, having a resolution of 1 micrometer for a visual field of 240×200 micrometers and being capable of taking 12 images per second. The aim is to carry out a precise visual examination of the outer surface of an internal organ, which examination will be described here as an optical biopsy. This is of course a non-limiting example.

Referring to FIGS. 1 and 2, the endoscope 1 has an elongate body which is introduced here into the abdomen 2 of a patient, here by way of a trocar 3. The endoscope 1 has a distal end 4 which is brought into immediate proximity with the outer surface of an internal organ 6. For this purpose, the endoscope is deformable in order to bring said end opposite the area of interest of the internal organ.

The distal end 4 here carries a probe 7, which is connected to its cable 8 extending inside the endoscope 1. The cable 8 forms a flexible connection of the probe 7 to the distal end 4 of the endoscope 1.

According to the invention, the distal end 4 is equipped with a foot 10 having a bearing part 11 for bearing against the internal organ 6, and a fixing part 12 for fixing to the distal end of the endoscope. Here, the bearing part 11 and the fixing part 12 are made in one piece, so as to form a foot in the general shape of a bell. The fixing part 12 is simply fitted onto the end of the endoscope.

Still according to the invention, the endoscope 1 is provided with means for moving the probe 7 relative to the foot 10, these means in this case being actuators 13 (here numbering three and being distributed uniformly at 120 degrees to one another), which extend between the foot 10 and the probe 7 in substantially convergent radial directions in order to permit a controlled movement of the probe 7 in directions transverse to the longitudinal axis X of the distal end 4 of the endoscope 1.

Here, the actuators 13 are symbolized schematically in the form of telescopic actuators which are articulated, via their ends, on the bearing part 11 of the foot 10 and on the probe 7. These actuators can be hydraulic or electro-mechanical jacks, for example. The length of the three actuators 13 can be varied here in order to move the probe opposite the internal organ. For this purpose, the three actuators 13 are controlled simultaneously in order to move the probe 7 on the desired trajectory.

The use of the endoscopic instrument of the invention is the following. The endoscope 1 is introduced into the abdomen of the patient so as to bring the foot 10 close to the internal organ. The foot is brought opposite the area to be examined, and the bearing part 11 of the foot 10 is applied against the internal organ with a pressure that is sufficient to avoid any movement of the bearing part 11 relative to the internal organ. It will be seen from FIG. 3b that the bearing of the foot 10 permits local deformation of the internal organ, such that the surface thereof to be examined is locally perpendicular to the longitudinal axis X, which is not the case with a traditional endoscope as illustrated in FIG. 3a.

With the foot 10 bearing on the internal organ, the actuators 13 are then controlled to move the probe 7 in such a way as to perform scanning of the area to be examined. Preferably, the scanning is organized such that each of the images taken by the probe 7 overlaps the preceding image by a rate of overlap of about 30%. Software for image recomposition recovers the images taken by the probe 7 in order to establish a particularly precise map of the area examined. The absence of movement of the internal organ relative to the foot makes it possible to ensure excellent overlap of the images taken by the probe 7.

According now to a second particular embodiment as illustrated in FIG. 4a, the bearing part 11 of the foot 10 is connected to the fixing part 12, for fixing to the endoscope 1, by a flexible part 14, which permits a relative movement between the distal end 4 of the endoscope 1 and the bearing part 11 of the foot 10. This arrangement permits a certain freedom of movement of the internal organ relative to the endoscope 1. However, the application of the bearing part 11 of the foot 10 on the internal organ prevents any relative movement of the bearing part 11 and of the internal organ. With the actuators 13 extending between the bearing part 11 and the probe 7, the position of the probe 7 relative to the internal organ therefore remains perfectly controlled. Thus, the flexible part 14 permits the transmission of an especially longitudinal force to the bearing part 11 in order to ensure that the foot 10 is pressed onto the internal organ with a pressure that is sufficient to prevent any relative movement of the foot 10 with respect to the internal organ, while allowing the possibility of an especially lateral movement of the bearing part 11 entrained by the internal organ when the latter moves. The flexible part 14 then deforms such that the distal end 4 of the endoscope 1 for its part remains immobile with respect to the internal organ.

The flexible part 14 can be made in one piece with the bearing part 11 and the fixing part 12, for example in the form of a bellows. The flexible part 14 can also be an element added between the bearing part 11 and the fixing part 12, for example an elastomeric ring. Alternatively, the flexible part can extend upstream of the foot, by being integrated in the endoscope itself, the foot then being connected rigidly, with the flexible part, to the end of the endoscope.

Figure 4C:
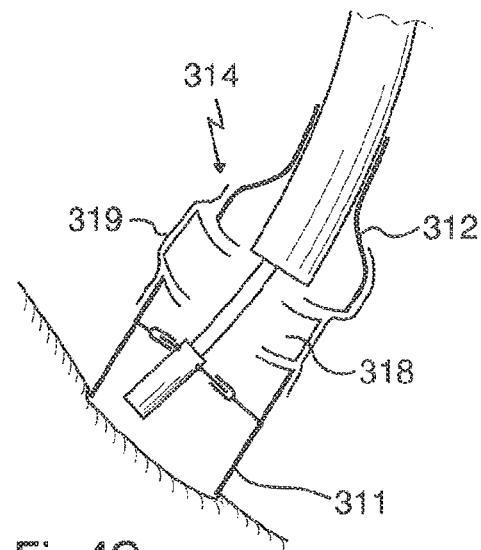
Figure 4D:
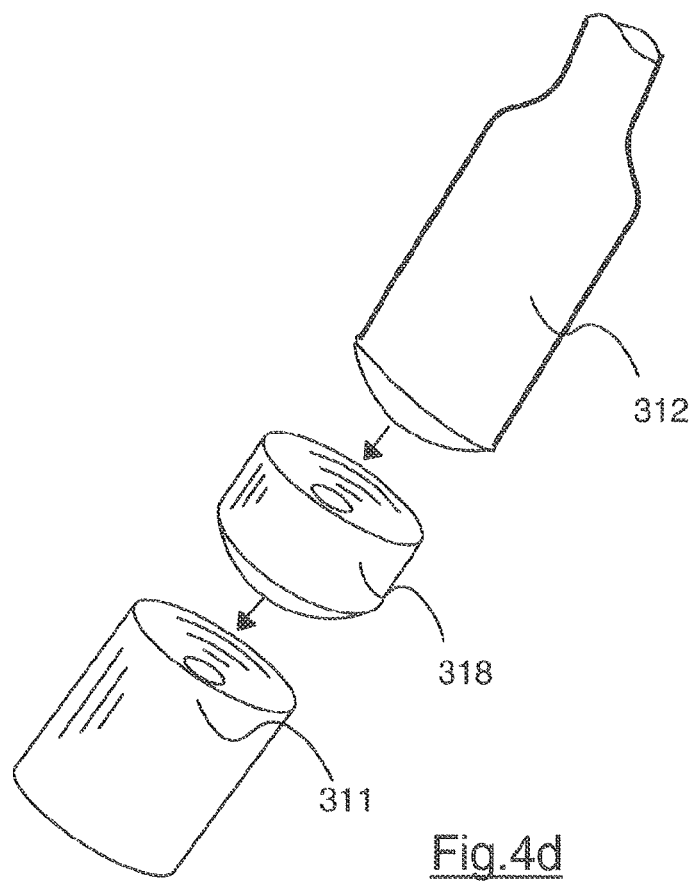
FIG. 4d is a partial exploded view of the instrument illustrated in FIGS. 4b and 4c.

According to another variant, and with reference to FIGS. 4*b* and 4*d*, the flexible part 314 has at least a first element providing a spherical support surface and made in one piece with the bearing part 311, and at least a second element providing a spherical support surface matching that of the first element, the second element being made in one piece with the fixing part 312. The flexible part 314 additionally has a sheath 319 made of elastic material and at least partly covering the first element and the second element. The elements of course have a hole at their center to permit passage of the tool.

For example, the first element has a concave spherical portion and the second element has a convex spherical portion. Here, the flexible part 314 has a third element 318 interposed between the bearing part 311 and the fixing part 312, the third element 318 having spherical support surfaces matching those of the first element and of the second element.

Thus, the flexible part 314 permits the transmission of an especially longitudinal force to the bearing part 311 in order to ensure that the foot 310 is pressed onto the internal organ with a pressure that is sufficient to prevent any relative movement of the foot 310 with respect to the internal organ, while allowing the possibility of an especially lateral movement of the bearing part 311 entrained by the internal organ when the latter moves. As is illustrated in FIG. 4*c*, the elements of the flexible part 314 then move with respect to one another in such a way that the second element, and therefore the distal end of the endoscope, remains immobile with respect to the internal organ.

According now to a third embodiment as illustrated in FIG. 5, the means of movement have two series of actuators 13 and 13' extending on two levels that are offset along the longitudinal axis X, making it possible to control with precision the angular orientation a of the working axis Y of the probe 7.

Here, the axes of the actuators are convergent on each of the levels. It will of course be possible to use more than two levels of actuators, for example if the tool manipulated by these actuators is flexible and if it is necessary to maintain it at several levels in order to ensure precise positioning of the end of the tool.

According now to a fourth embodiment as illustrated in FIG. 6, the foot is now in the form of a tripod 110 with three legs 111 having ends that bear against the internal organ and that each receive the end of one of the actuators 113, which here extend in convergent directions.

Preferably, the legs 111 are flexible and are connected to means for retracting them inside the endoscope, so as to arrive at the configuration illustrated in FIG. 7 in which the foot 110 is retracted in the endoscope 101. In this configuration, the actuators 113 are folded back along the legs 111.

To do this, it suffices, for example, to pull the cable 108 of the probe 107. This retracted position greatly facilitates the introduction of the endoscope into the body of the patient. After the distal end of the endoscope has been introduced and brought into proximity with the internal organ, the foot 110 is deployed, here by pushing back the probe 107 via its cable 108 (if the latter is sufficiently rigid). The foot 110 is then ready to be applied against the internal organ. If the cable 108 is unable to perform the function of deployment/retraction of the foot 110, specific means of actuation will be provided to ensure these operations, for example a tubular sheath, which is mounted inside the endoscope so as to slide therein and at the end of which the legs 111 are fixed.

According now to a fifth particular embodiment of the endoscopic instrument as illustrated in FIG. 8, the endoscope 201 carries a foot 210 and is equipped with actuators 213 for moving the probe 207. However, the actuators 213 here extend between the probe 207 and the end of the endoscope 201.

This arrangement makes it easier to confer movements on the tool, which are no longer just transverse movements but also longitudinal movements. This feature is particularly useful in the case where the tool is a biopsy needle or if the probe has to penetrate the internal organ.

Of course, the invention is not limited to what has just been described, and instead it encompasses any variant falling within the scope defined by the claims. In particular, the functional features described here, in connection with the description of the various embodiments of the invention that are illustrated, can of course be combined with one another.

Endoscopic instrument is to be understood in the broad sense of the term, and it includes instruments such as bronchoscopes, gastroscopes, rectoscopes, laparoscopes, arthroscopes, etc.

Although the tool carried here by the endoscopic instrument is an imaging probe, the invention is of course not limited to this type of tool. The invention also applies to an endoscopic instrument carrying a treatment tool (for example an abrasion tool or a tool for delivering a medicament), a surgical tool (a needle, a blade, forceps, etc.), or any other tool.

Of course, the invention is not limited to the use of telescopic actuators, nor to the number of actuators mentioned, for moving the tool of the instrument with respect to the foot. Any controllable means of movement may be envisioned within the scope of the invention, provided that it permits movements of the tool in at least directions that are transverse to a longitudinal axis of the distal end of the endoscopic instrument. For example, it will be possible to use actuators that are electro-mechanical, hydraulic, piezo-electric or based on elements made of shape-memory alloy. It will also be possible for the tool to be rigidly connected to a sleeve that is sensitive to the action of a peripheral electro-magnetic actuator extending around the sleeve and able to attract the sleeve in one or other transverse direction.

Finally, although the probe is here connected to the distal end of the endoscope via its cable allowing a freedom of movement of the probe with respect to the foot, it will of course be possible to provide any other type of connection of the tool to the endoscope. For example, the tool can be mounted on the end of an arm which is articulated on the distal end of the endoscope. The tool can also be rigidly connected to the endoscope solely via the means of movement.

In the fourth embodiment as illustrated in FIG. 6, the legs forming a bearing part of the foot are independent of one another. Alternatively, it will of course be possible for the legs to be connected to one another, for example by a flexible web.

The invention claimed is:

1. An endoscopic instrument (1) comprising an elongate body with a distal end (4) designed to be introduced into the body of the patient so as to come into proximity with an internal organ, the distal end carrying a tool (7) for intervention on the internal organ, the endoscopic instrument comprising a foot (10, 110) rigidly connected to the distal end and extending from the distal end, the foot having a terminal end opposite to an end of the foot that connects the foot to the distal end of the elongate body, the foot designed to bear on the internal organ, and also controllable means of movement (13, 13', 113) for conferring movements on the tool, at least in directions transverse to a longitudinal axis (X) of the distal end of the endoscopic instrument, when the foot is bearing against the internal organ, wherein the means of movement have at least one actuator (13, 13', 113, 213), which is coupled to the tool and which is arranged entirely within the foot so as not to extend beyond the terminal end of the foot;

wherein the actuator is contained within the foot at a location no more proximal than the distal most end of the elongated body of the endoscopic instrument; and wherein the tool is configured so as not to extend beyond the terminal end of the foot.

2. The endoscopic instrument as claimed in claim 1, in which the actuator (213) extends between the distal end of the endoscopic instrument and the tool (207).

3. The endoscopic instrument as claimed in claim 1, in which the actuator extends between the foot (10; 110) and the tool (7; 107).

4. The endoscopic instrument as claimed in claim 1, in which the means of movement have a plurality of actuators (13, 13', 113) extending in convergent directions between the foot and the tool.

5. The endoscopic instrument as claimed in claim 1, in which the means of movement have at least two series of actuators (13, 13') arranged on respective offset levels, so as to extend, on each of the levels, in convergent directions between the foot and the tool.

6. The endoscopic instrument as claimed in claim 1, in which the foot has a bearing part (11) connected to a fixing part (12) for fixing to the endoscope, the bearing and fixing parts being made in one piece.

7. The endoscopic instrument as claimed in claim 1, in which the foot has a bearing part (11) connected to a fixing part (12) by a flexible part (14).

8. The endoscopic instrument as claimed in claim 7, in which the flexible part has:
at least a first element providing a spherical support surface and made in one piece with the bearing part (311), and at least a second element providing a spherical support surface matching that of the first element, the second element being made in one piece with the fixing part (312);
a sheath (319) made of elastic material and at least partly covering the first element and the second element.

9. The endoscopic instrument as claimed in claim 1, in which the foot (110) has a plurality of legs (111) with ends that form a bearing part of the foot.

10. The endoscopic instrument as claimed in claim 9, in which at least the ends of the legs forming a bearing part of the foot are independent of one another.

11. The endoscopic instrument as claimed in claim 9, in which the legs (111) are retractable inside the endoscopic instrument.

12. The endoscopic instrument as claimed in claim 1, wherein the at least one actuator is connected to an interior portion of the foot.

13. An endoscopic instrument having an elongate body with a distal end configured to be introduced into the body of the patient so as to come into proximity with an internal organ, the distal end carrying a tool for intervention on the internal organ, the endoscopic instrument having a foot rigidly connected to the distal end and extending from the distal end, the foot having a terminal end opposite to an end of the foot that connects the foot to the distal end of the elongate body, the foot designed to bear on the internal organ, and controllable means of movement for conferring movements on the tool, at least in directions transverse to a longitudinal axis (X) of the distal end of the endoscopic instrument, when the foot is bearing against the internal organ, wherein the means of movement have at least one actuator that is coupled to the tool and that is arranged entirely within the foot so as not to extend beyond the terminal end of the foot, the tool also arranged so as not to extend beyond the terminal end of the foot; and wherein the actuator is a telescopic actuator connected to an interior portion of the foot and articulated by a hydraulic or electromechanical jack; and and wherein the actuator is contained within the foot at a location no more proximal than the distal most end of the elongated body of the endoscope.

* * * * *